(12) United States Patent
Carter et al.

(10) Patent No.: US 8,492,550 B2
(45) Date of Patent: Jul. 23, 2013

(54) HYDROXYALKANYL AMIDES AS MODULATORS OF CHEMOKINE RECEPTOR ACTIVITY

(75) Inventors: Percy H. Carter, Princeton, NJ (US); Lyndon A. M. Cornelius, Jackson, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 166 days.

(21) Appl. No.: 12/920,668

(22) PCT Filed: Mar. 5, 2009

(86) PCT No.: PCT/US2009/036120
§ 371 (c)(1),
(2), (4) Date: Sep. 2, 2010

(87) PCT Pub. No.: WO2009/111607
PCT Pub. Date: Sep. 11, 2009

(65) Prior Publication Data
US 2011/0009452 A1    Jan. 13, 2011

Related U.S. Application Data

(60) Provisional application No. 61/034,637, filed on Mar. 7, 2008.

(51) Int. Cl.
*C07D 211/20* (2006.01)
*A61K 31/451* (2006.01)

(52) U.S. Cl.
USPC .......................................... 546/234; 514/331

(58) Field of Classification Search
USPC ........................................................ 546/234
See application file for complete search history.

(56) References Cited

U.S. PATENT DOCUMENTS 6,323,223 B1 * 11/2001 Gong et al. .................... 514/331
6,624,309 B1 * 9/2003 Lloyd et al. .................... 548/131

FOREIGN PATENT DOCUMENTS

WO    WO 2006081289 A2 * 8/2006

OTHER PUBLICATIONS

Ting et. al. "The synthesis of substituted bipiperidine amide compounds as CCR3 ligands: Antagonists versus agonists" Bioorganic & Medicinal Chemistry Letters 2005 15, 3020-3023.*
Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).
Barnes, D.A. et al., "Polyclonal Antibody Directed Against Human RANTES Ameliorates Disease in the Lewis Rat Adjuvant-induced Arthritis Model", J. Clin. Invest., vol. 101, pp. 2910-2919 (1998).
Beck, L.A. et al., "Cutaneous Injection of RANTES Causes Eosinophil Recruitment: Comparison of Nonallergic and Allergic Human Subjects", The Journal of Immunology, vol. 159, pp. 2962-2972 (1997).
Bonini, J.A. et al., "Cloning, Expression, and Chromosomal Mapping of a Novel Human CC-Chemokine Receptor (CCR10) that Displays High-Affinity Binding for MCP-1 and MCP-3", DNA and Cell Biology, vol. 16, No. 10, pp. 1249-1256 (1997).
Carson, K.G. et al., "CCR1 Antagonists", Annual Reports in Medicinal Chemistry, vol. 39, pp. 149-158 (2004).
Carter, P.H., "Chemokine receptor antagonism as an approach to anti-inflammatory therapy: 'just right' or plain wrong?", Current Opinion in Chemical Biology, vol. 6, pp. 510-525 (2002).
Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).
Chintalacharuvu, S.R. et al., "An essential role for CCL3 in the development of collagen antibody-induced arthritis", Immunology Letters, vol. 100, pp. 202-204 (2005).
Combadiere, C. et al., "Cloning and Functional Expression of a Human Eosinophil CC Chemokine Receptor", The Journal of Biological Chemistry, vol. 270, No. 27, pp. 16491-16494 (1995).
Cook, D.N. et al., "Requirement of MIP-1α for an Inflammatory Response to Viral Infection", Science, vol. 269, pp. 1583-1585 (1995).
Gao, J.-L. et al., "Impaired Host Defense, Hematopoiesis, Granulomatous Inflammation and Type 1-Type 2 Cytokine Balance in Mice Lacking CC Chemokine Receptor 1", The Journal of Experimental Medicine, vol. 185, No. 11, pp. 1959-1968 (1997).
Horuk, R., "Molecular properties of the chemokine receptor family", Trends in Pharmacological Sciences, vol. 15, pp. 159-165 (1994).
Karpus, W.J. et al., "An Important Role for the Chemokine Macrophage Inflammatory Protein-1α in the Pathogenesis of the T Cell-Mediated Autoimmune Disease, Experimental Autoimmune Encephalomyelitis", The Journal of Immunology, vol. 155, pp. 5003-5010 (1995).
Kasama, T. et al., "Interleukin-10 Expression and Chemokine Regulation During the Evolution of Murine Type II Collagen-induced Arthritis", J. Clin. Invest., vol. 95, pp. 2868-2876 (1995).
Koch, A.E. et al., "Macrophage Inflammatory Protein-1α: A Novel Chemotactic Cytokine for Macrophages in Rheumatoid Arthritis", J. Clin. Invest., vol. 93, pp. 921-928 (1994).

(Continued)

Primary Examiner — David K O Dell
(74) Attorney, Agent, or Firm — Terence J. Bogie

(57) ABSTRACT

The application describes modulators of MIP-1α or CCR-1 of the formula (I) or stereoisomers or prodrugs or pharmaceutically acceptable salts thereof, wherein ring A, T, V, $R_1$, $R_2$ and $R_5$, are defined herein. In addition, methods of treating and preventing inflammatory diseases such as asthma and allergic diseases, as well as autoimmune pathologies such as rheumatoid arthritis and transplant rejection using modulators of formula (I) are disclosed.

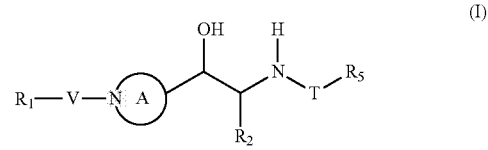

2 Claims, No Drawings

OTHER PUBLICATIONS

Lee, S.C. et al., "Cutaneous Injection of Human Subjects with Macrophage Inflammatory Protein-1α Induces Significant Recruitment of Neutrophils and Monocytes", The Journal of Immunology, vol. 164, pp. 3392-3401 (2000).

Luster, A.D., "Chemokines—Chemotactic Cytokines that Mediate Inflammation", The New England Journal of Medicine, vol. 338, No. 7, pp. 436-445 (1998).

Napolitano, M. et al., "Molecular Cloning of TER1, a Chemokine Receptor-Like Gene Expressed by Lymphoid Tissues", The Journal of Immunology, vol. 157, pp. 2759-2763 (1996).

Neote, K. et al., "Molecular Cloning, Functional Expression, and Signaling Characteristics of a C-C Chemokine Receptor", Cell, vol. 72, pp. 415-425 (1993).

Pease, J.E. et al., "CCR1 antagonists in clinical development", Expert Opin. Investig. Drugs, vol. 14, No. 7, pp. 785-796 (2005).

Plater-Zyberk, C. et al., "Effect of a CC chemokine receptor antagonist on collagen induced arthritis in DBA/1 mice", Immunology Letters, vol. 57, pp. 117-120 (1997).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Premack, B.A. et al., "Chemokine receptors: Gateways to inflammation and infection", Nature Medicine, vol. 2, No. 11, pp. 1174-1178 (1996).

Rollins, B.J., "Chemokines", Blood, vol. 90, No. 3, pp. 909-928 (1997).

Samson, M. et al., "Molecular Cloning and Functional Expression of a New Human CC-Chemokine Receptor Gene", Biochemistry, vol. 35, No. 11, pp. 3362-3367 (1996).

Saunders, J. et al., "Opportunities for novel therapeutic agents acting at chemokine receptors", Drug Discovery Today, vol. 4, No. 2, pp. 80-92 (1999).

Schweickart, V.L. et al., "CCR11 is a Functional Receptor for the Monocyte Chemoattractant Protein Family of Chemokines", The Journal of Biological Chemistry, vol. 275, No. 13, pp. 9550-9556 (2000), and vol. 276, No. 1, p. 856 (2001) (errata sheet).

Shahara, S. et al., "Amelioration of Rat Adjuvant-Induced Arthritis by Met-RANTES", Arthritis & Rheumatism, vol. 52, No. 6, pp. 1907-1919 (2005).

Trivedi, B.K. et al., Chapter 17: "Chemokines: Targets for Novel Therapeutics", Annual Reports in Medicinal Chemistry, vol. 35, Academic Press, publ., pp. 191-200 (2000).

Wells, T.N.C. et al., "Plagiarism of the host immune system: lessons about chemokine immunology from viruses", Current Opinion in Biotechnology, vol. 8, pp. 741-748 (1997).

Yoshie, O. et al., "Novel lymphocyte-specific CC chemokines and their receptors", Journal of Leukocyte Biology, vol. 62, pp. 634-644 (1997).

Zlotnik, A. et al., "Chemokines: A New Classification System and Their Role in Immunity", Immunity, vol. 12, pp. 121-127 (2000).

* cited by examiner

HYDROXYALKANYL AMIDES AS MODULATORS OF CHEMOKINE RECEPTOR ACTIVITY

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.*, 338: 436-445 (1998) and Rollins, *Blood*, 90:909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.*, 15:159-165 (1994)) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik et al., *Immunity*, 12:121 (2000)): CCR-1 (or "CKR-1" or "CC-CKR-1") [MIP-1α, MCP-3, MCP-4, RANTES] (Neote et al., *Cell*, 72:415-425 (1993), and Luster, *New Eng. J. Med.*, 338:436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA*, 91:2752-2756 (1994), and Luster, *New Eng. J. Med.*, 338: 436-445 (1998)); CCR-3 (or "CKR-3" or "CC-CKR-3") [eotaxin-1, eotaxin-2, RANTES, MCP-3, MCP-4] (Combadiere et al., *J. Biol. Chem.*, 270:16491-16494 (1995), and Luster, *New Eng. J. Med.*, 338:436-445 (1998)); CCR-4 (or "CKR-4" or "CC-CKR-4") [TARC, MDC] (Power et al., *J. Biol. Chem.*, 270:19495-19500 (1995), and Luster, *New Eng. J. Med.*, 338: 436-445 (1998)); CCR-5 (or "CKR-5" OR "CC-CKR-5") [MIP-1α, RANTES, MIP-1β] (Samson et al., *Biochemistry*, 35:3362-3367 (1996)); CCR-6 (or "CKR-6" or "CC-CKR-6") [LARC] (Baba et al., *J. Biol. Chem.*, 272:14893-14898 (1997)); CCR-7 (or "CKR-7" or "CC-CKR-7") [ELC] (Yoshie et al., *J. Leukoc. Biol.*, 62:634-644 (1997)); CCR-8 (or "CKR-8" or "CC-CKR-8") [1-309] (Napolitano et al., *J. Immunol.*, 157:2759-2763 (1996)); CCR-10 (or "CKR-10" or "CC-CKR-10") [MCP-1, MCP-3] (Bonini et al., *DNA and Cell Biol.*, 16:1249-1256 (1997)); and CCR-11 [MCP-1, MCP-2, and MCP-4] (Schweickart et al., *J. Biol. Chem.*, 275:9550 (2000)).

In addition to the mammalian chemokine receptors, mammalian cytomegaloviruses, herpesviruses and poxviruses have been shown to express, in infected cells, proteins with the binding properties of chemokine receptors (reviewed in: Wells et al., *Curr. Opin. Biotech.*, 8:741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., *Curr. Opin. Chem. Biol.*, 6:510 (2002); Trivedi et al., *Ann. Reports Med. Chem.*, 35:191 (2000); Saunders et al., *Drug Disc. Today*, 4:80 (1999); Premack et al., *Nature Medicine*, 2:1174 (1996)). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.*, 164:3392-3401 (2000)).

Demonstration of the importance of the MIP-1α/CCR-1 interaction has been provided by experiments with genetically modified mice. MIP-1α−/− mice had normal numbers of leukocytes, but were unable to recruit monocytes into sites of viral inflammation after immune challenge (Cook, D. et al., *Science.*, 269:1583-1585 (1995)). Recently, MIP-1α−/− mice were shown to be resistant to collagen antibody induced arthritis (Chintalacharuvu, S. R., *Immun. Lett.*, 202-204 (2005)). Likewise, CCR-1−/− mice were unable to recruit neutrophils when challenged with MIP-1α in vivo; moreover, the peripheral blood neutrophils of CCR-1 null mice did not migrate in response to MIP-1α (Gao, B. et al., *J. Exp. Med.*, 185:1959-1968 (1997)), thereby demonstrating the specificity of the MIP-1α/CCR-1 interaction. The viability and generally normal health of the MIP-1α−/− and CCR-1−/− animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis (Koch, A. et al., *J. Clin. Invest.*, 93:921-928 (1994)). Moreover, several studies have demonstrated the potential therapeutic value of antagonism of the MIP-1α/CCR1 interaction in treating rheumatoid arthritis (Pease, J. E. et al., *Expert Opin. Invest. Drugs*, 14:785-796 (2005)).

An antibody to MIP-1α was shown to ameliorate experimental autoimmune encepahlomytis (EAE), a model of multiple sclerosis, in mice (Karpus, W. J. et al., *J. Immun.*, 5003-5010 (1995)). Likewise, inflammatory disease symptoms could be controlled via direct administration of antibodies for MIP-1α to mice with collagen-induced arthritis (Lukacs, N. W. et al., *J. Clin. Invest.*, 95:2868-2876 (1995)).

It should also be noted that CCR-1 is also the receptor for the chemokines RANTES, MCP-3, HCC-1, Lkn-1/HCC-2, HCC-4, and MPIF-1 (Carter, P. H., *Curr. Opin. Chem. Biol.*, 6:510-525 (2002)). Since it is presumed that the new compounds of formula (I) described herein antagonize MIP-1α by binding to the CCR-1 receptor, it may be that these compounds of formula (I) are also effective antagonists of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

For example, demonstration of the chemotactic properties of RANTES in humans has been provided experimentally. Human subjects, when injected intradermally with RANTES, experienced an influx of eosinophils to the site of injection (Beck, L. A. et al., *J. Immun.*, 159:2962-2972 (1997)). Likewise, a RANTES antibody has demonstrated the ability to ameliorate the symptoms of disease in the rat Adjuvant induced arthritis (AIA) model (Barnes, D. A. et al., *J. Clin Invest.*, 101:2910-2919 (1998)). Similar results were obtained when using a peptide derived antagonist of the RANTES/CCR-1 interaction in both the rat AIA (Shahrara, S. et al., *Arthritis & Rheum.*, 52:1907-1919 (2005)) and the mouse CIA (Plater-Zyberk, C. et al., *Imm. Lett.*, 57:117-120 (1997)) disease models of joint inflammation.

Recently, a number of groups have described the development of small molecule antagonists of MIP-1α (reviewed in: Carson, K. G. et al., *Ann. Reports Med. Chem.*, 39:149-158 (2004)).

SUMMARY OF THE INVENTION

Accordingly, the present invention provides novel antagonists or partial agonists/antagonists of MIP-1α or CCR-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel hydroxyalkanyl amide derivatives for use in therapy.

The present invention provides the use of novel hydroxyalkanyl amide derivatives for the manufacture of a medicament for the treatment of inflammatory diseases.

These and other features of the invention, which will become apparent during the following detailed description, have been achieved by the inventors' discovery that compounds of formula (I):

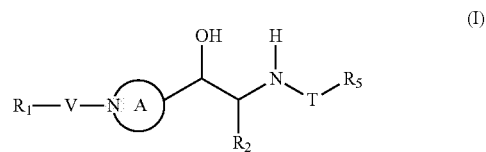

or stereoisomers or prodrugs or pharmaceutically acceptable salts thereof, wherein ring A, T, V, $R_1$, $R_2$ and $R_5$, are defined below, are effective modulators of MIP-1α and chemokine activity.

DETAILED DESCRIPTION OF THE PRESENT INVENTION

In one embodiment, the present invention provides novel compounds of formula (I):

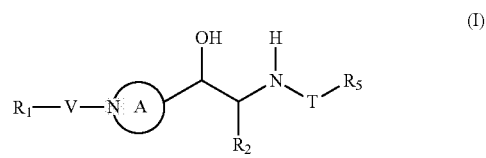

or stereoisomers or prodrugs or pharmaceutically acceptable salt forms thereof, wherein:

the dashed line represents an optional double bond;

Ring A is

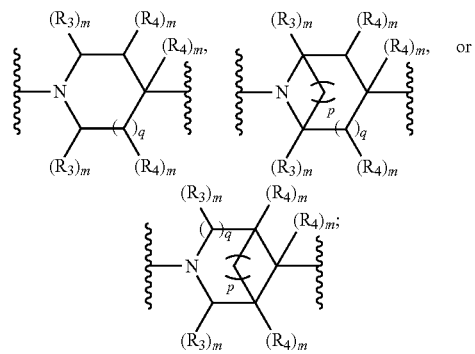

T is

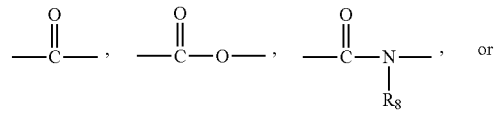

-continued $$-\overset{O}{\underset{\underset{O}{\|}}{\overset{\|}{S}}}-;$$

V is a bond, $-(CR_8R_8)_p-$, $$-\overset{O}{\overset{\|}{C}}-,\quad -\overset{O}{\overset{\|}{C}}-O-,\quad -\overset{O}{\overset{\|}{C}}-\overset{}{\underset{R_8}{N}}-,\quad \text{or}$$

$$-\overset{O}{\underset{\underset{O}{\|}}{\overset{\|}{S}}}-;$$

$R_1$ is aryl or heteroaryl, both of which may be optionally substituted with one or more $R_{1a}$;

$R_{1a}$ is halo, —CN, alkyl, haloalkyl, —O-alkyl or —O-haloalkyl;

$R_2$ is alkyl, cycloalkyl, cycloalkylalkyl, or alkenyl, wherein the alkyl may be optionally substituted with —OH;

$R_3$, at each occurrence, is alkyl; or any two $R_3$'s attached to the same carbon atom may form a 3- to 6-membered ring;

$R_4$, at each occurrence, is F, alkyl, —$OR_9$ or —$NR_9R_9$; or any two alkyl $R_4$'s attached to the same carbon atom may form a 3- to 6-membered ring;

$R_5$ is alkyl, cycloalkyl, aryl, heterocyclyl or heteroaryl, all of which may be optionally substituted with one or more $R_{5a}$;

$R_{5a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$($CF_2$)$_r$$CF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2$($CF_2$)$_r$$CF_3$, —C(=O)$_2$($CR_8R_8$)$_r$$R_{10}$, —$NR_9$C(=O)H, —$NR_9$C(=O)($CR_8R_8$)$_r$$R_{10}$, —$NR_9$C(=O)$NR_9R_9$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C(=O)$OR_8$, —$NR_9$S(O$_2$)$R_8$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{5b}$;

$R_{5b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$($CF_2$)$_r$$CF_3$, —C(=O)$NR_9$S(O)$_2R_6$, —S(O)$_2NR_9$C(=O)$OR_6$, —S(O)$_2$$NR_9$C(=O)$NR_9R_9$, —C(=O)$NR_9$S(O)$_2$($CF_2$)$_r$$CF_3$, —C(=O)($CR_8R_8$)$_r$$R_{10}$, —$NR_9$C(=O)H, —$NR_9$C(=O)($CR_8R_8$)$_r$$R_{10}$, —$NR_9$C(=O)$NR_9R_9$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C(=O)$OR_8$, —$NR_9$S(O$_2$)$R_8$, aryloxy or arylalkyl;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl, —S(O)$_2R_{15}$, —C(=O)$R_{15}$, —C(=O)$NR_8R_{15}$, —C(=O)$OR_{15}$ or heterocyclylalkyl, wherein the aryl, arylalkyl, heteroaryl, heteroarylalkyl, heterocyclyl or heterocyclylalkyl may be optionally substituted with one or more $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$H$_2$, —C(=O)$NR_{14}R_{14}$, —$NR_{14}R_{14}$, —S(O)$_2NR_{14}R_{14}$, —$NR_{14}$S(O)$_2$($CF_2$)$_r$$CF_3$, —C(=O)$NR_{14}$S(O)$_2R_6$, —S(O)$_2NR_{14}$C(=O)$OR_6$, —S(O)$_2NR_{14}$C(=O)$NR_{14}R_{14}$, —C(=O)$NR_{14}$S(O)$_2$($CF_2$)$_r$$CF_3$, —C(=O)($CR_8R_8$)$_r$$R_{14}$, —$NR_{14}$C(=O)H, —$NR_{14}$C(=O)($CR_8R_8$)$_r$$R_{14}$, —OC(=O)($CR_8R_8$)$_r$$R_{14}$, —C(=$NR_{14}$)$NR_{14}R_{14}$, —NHC(=$NR_{14}$)$NR_{14}R_{14}$, —S(=O)($CR_8R_8$)$_r$$R_{14}$, —S(O)$_2$($CR_8R_8$)$_r$$R_{14}$, —$NR_{14}$C(=O)$OR_8$, —$NR_{14}$S(O$_2$)$R_8$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with one or more $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$H$_2$, —C(=O)$NR_{14}R_{14}$, —$NR_{14}R_{14}$, —S(O)$_2NR_{14}R_{14}$, —$NR_{14}$S(O)$_2$($CF_2$)$_r$$CF_3$, —C(=O)$NR_{14}$S(O)$_2R_6$, —S(O)$_2NR_{14}$C(=O)$OR_6$, —S(O)$_2NR_{14}$C(=O)$NR_{14}R_{14}$, —C(=O)$NR_{14}$S(O)$_2$($CF_2$)$_r$$CF_3$, —C(=O)($CR_8R_8$)$_r$$R_{14}$, —$NR_{14}$C(=O)H, —$NR_{14}$C(=O)($CR_8R_8$)$_r$$R_{14}$, —OC(=O)($CR_8R_8$)$_r$$R_{14}$, —C(=$NR_{14}$)$NR_{14}R_{14}$, —NHC(=$NR_{14}$)$NR_{14}R_{14}$, —S(=O)($CR_8R_8$)$_r$$R_{14}$, —S(O)$_2$($CR_8R_8$)$_r$$R_{14}$, —$NR_{14}$C(=O)$OR_8$, —$NR_{14}$S(O$_2$)$R_8$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl;

m, at each occurrence, is 0-2;

p is 1 or 2;

q is 0-2; and r, at each occurrence, is 0-5.

In another embodiment, compounds of the present invention, or a stereoisomer or pharmaceutically acceptable salt from thereof, are those in which the compound is a compound of formula (Ia):

(Ia)

In another embodiment, compounds of the present invention, or a stereoisomer or pharmaceutically acceptable salt from thereof, are those in which the compound is a compound of formula (Ib):

(Ib)

in which $R_1$ is phenyl optionally substituted with one or more $R_{1a}$; V is a bond; $R_2$ is alkyl, optionally substituted with OH; T is —C(O)— and —C(O)NH—; and $R_5$ is alkyl, cycloalkyl, aryl, heterocyclyl or heteroaryl, all of which may be optionally substituted with one or more $R_{5a}$.

In another embodiment, compounds of the present invention, or a stereoisomer or pharmaceutically acceptable salt from thereof, are those in which the compound is a compound of formula (Ic):

(Ic)

in which $R_1$ is phenyl optionally substituted with one or more $R_{1a}$.

In yet another embodiment, compounds of the present invention, or a stereoisomer or pharmaceutically acceptable salt from thereof, are those in which:

Ring A is

T is

V is a bond, —$(CR_8R_8)_p$—, $R_1$ is aryl or heteroaryl, both of which may be optionally substituted with one or more $R_{1a}$;

$R_{1a}$ is halo, —CN, alkyl, haloalkyl, —O-alkyl or —O-haloalkyl;

$R_2$ is alkyl, cycloalkyl, cycloalkylalkyl, or alkenyl, wherein the alkyl may be optionally substituted with —OH;

$R_3$, at each occurrence, is alkyl; or any two $R_3$'s attached to the same carbon atom may form a 3- to 6-membered ring;

$R_4$, at each occurrence, is F, alkyl, —$OR_9$ or —$NR_9R_9$; or any two alkyl $R_4$'s attached to the same carbon atom may form a 3- to 6-membered ring;

$R_5$ is alkyl, cycloalkyl, aryl, heterocyclyl or heteroaryl, all of which may be optionally substituted with one or more $R_{5a}$;

$R_{5a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —S(O)$_3$H, —P(O)$_3H_2$, —C(=O)NR$_9R_9$, —NR$_9R_9$, —S(O)$_2$NR$_9R_9$, —NR$_9$S(O)$_2(CF_2)_rCF_3$, —C(=O)NR$_9$S(O)$_2R_6$, —S(O)$_2$NR$_9$C(=O)OR$_6$, —S(O)$_2$NR$_9$C(=O)NR$_9R_9$, —C(=O)NR$_9$S(O)$_2(CF_2)_rCF_3$, —C(=O)$(CR_8R_8)_rR_{10}$, —NR$_9$C(=O)H, —NR$_9$C(=O)$(CR_8R_8)_rR_{10}$, —NR$_9$C(=O)NR$_9R_9$, —OC(=O)$(CR_8R_8)_rR_{10}$, —NHC(=NR$_{14}$)NR$_{14}R_{14}$, —S(=O)$(CR_8R_8)_rR_{10}$, —S(O)$_2(CR_8R_8)_rR_{10}$, —NR$_9$C(=O)OR$_8$, —NR$_9$S(O$_2$)R$_8$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{5b}$, $R_{5b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —S(O)$_3$H, —P(O)$_3H_2$, —C(=O)NR$_9R_9$, —NR$_9R_9$, —S(O)$_2$NR$_9R_9$, —NR$_9$S(O)$_2(CF_2)_rCF_3$, —C(=O)NR$_9$S(O)$_2R_6$, —S(O)$_2$NR$_9$C(=O)OR$_6$, —S(O)$_2$NR$_9$C(=O)NR$_9R_9$, —C(=O)NR$_9$S(O)$_2(CF_2)_rCF_3$, —C(=O)$(CR_8R_8)_rR_{10}$, —NR$_9$C(=O)H, —NR$_9$C(=O)$(CR_8R_8)_rR_{10}$, —NR$_9$C(=O)NR$_9R_9$, —OC(=O)$(CR_8R_8)_rR_{10}$, —NHC(=NR$_{14}$)NR$_{14}R_{14}$, —S(=O)$(CR_8R_8)_rR_{10}$, —S(O)$_2(CR_8R_8)_rR_{10}$, —NR$_9$C(=O)OR$_8$, —NR$_9$S(O$_2$)R$_8$, aryloxy or arylalkyl;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl, —S(O)$_2R_{15}$, —C(=O)R$_{15}$, —C(=O)NR$_8R_{15}$, —C(=O)OR$_{15}$ or heterocyclylalkyl, wherein the aryl, arylalkyl, heteroaryl, heteroarylalkyl, heterocyclyl or heterocyclylalkyl may be optionally substituted with one or more $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S(O)$_3$H, —P(O)$_3H_2$, —C(=O)NR$_{14}R_{14}$, —NR$_{14}R_{14}$, —S(O)$_2$NR$_{14}R_{14}$, —NR$_{14}$S(O)$_2(CF_2)_rCF_3$, —C(=O)NR$_{14}$S(O)$_2R_6$, —S(O)$_2$NR$_{14}$C(=O)OR$_6$, —S(O)$_2$NR$_{14}$C(=O)NR$_{14}R_{14}$, —C(=O)NR$_{14}$S(O)$_2(CF_2)_rCF_3$, —C(=O)$(CR_8R_8)_rR_{14}$, —NR$_{14}$C(=O)H, —NR$_{14}$C(=O)$(CR_8R_8)_rR_{14}$, —OC(=O)$(CR_8R_8)_rR_{14}$, —NHC(=NR$_{14}$)NR$_{14}R_{14}$, —S(=O)$(CR_8R_8)_rR_{14}$, —S(O)$_2(CR_8R_8)_rR_{14}$, —NR$_{14}$C(=O)OR$_8$, —NR$_{14}$S(O$_2$)R$_8$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with one or more R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{14}$, at each occurrence, is independently selected from hydrogen, alkyl, cycloalkyl or phenyl;

R$_{15}$, at each occurrence, is independently selected from alkyl, cycloalkyl or phenyl;

m, at each occurrence, is 0-2;

p is 1 or 2;

q is 0-2; and r, at each occurrence, is 0-4.

In still yet another embodiment, compounds of the present invention, or a stereoisomer or pharmaceutically acceptable salt from thereof, are those in which:

Ring A is

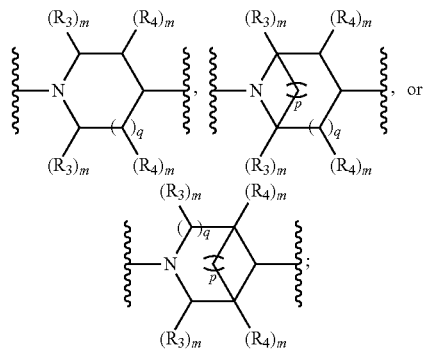

T is 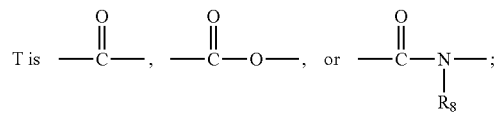

V is a bond, —(CR$_8$R$_8$)$_p$—,

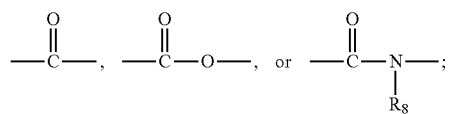

R$_1$ is aryl or heteroaryl, both of which may be optionally substituted with one or more R$_{1a}$;

R$_{1a}$ is halo, —CN, alkyl, haloalkyl, —O-alkyl or —O-haloalkyl;

R$_2$ is alkyl, cycloalkyl or alkenyl, wherein the alkyl may be optionally substituted with —OH;

R$_3$, at each occurrence, is alkyl; or any two R$_3$'s attached to the same carbon atom may form a 3- to 6-membered ring;

R$_4$, at each occurrence, is F, alkyl, —OR$_9$ or —NR$_9$R$_9$; or any two alkyl R$_4$'s attached to the same carbon atom may form a 3- to 6-membered ring;

R$_5$ is alkyl, cycloalkyl, aryl, heterocyclyl or heteroaryl, all of which may be optionally substituted with one or more R$_{5a}$;

R$_{5a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$$_5$—C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_{35}$—C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more R$_{5b}$;

R$_{5b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, —OC(=O)(CR$_8$R$_8$)$_r$R$_{10}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl, —S(O)$_2$R$_{15}$, —C(=O)R$_{15}$, —C(=O)NR$_8$R$_{15}$, —C(=O)OR$_{15}$ or heterocyclylalkyl, wherein the aryl, arylalkyl, heteroaryl, heteroarylalkyl, heterocyclyl or heterocyclylalkyl may be optionally substituted with one or more R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with one or more $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2(CF_2)_rCF_3$, —C(=O)$NR_{14}S(O)_2R_6$, —$S(O)_2NR_{14}C(=O)OR_6$, —$S(O)_2NR_{14}C(=O)NR_{14}R_{14}$, —C(=O)$NR_{14}S(O)_2(CF_2)_rCF_3$, —C(=O)(CR_8R_8)_rR_{14}$, —$NR_{14}C(=O)H$, —$NR_{14}C(=O)(CR_8R_8)_rR_{14}$, —OC(=O)(CR_8R_8)_rR_{14}$, —S(=O)(CR_8R_8)_rR_{14}$, —S(O)_2(CR_8R_8)_rR_{14}$, —$NR_{14}C(=O)OR_8$, —$NR_{14}S(O_2)R_8$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl;

m, at each occurrence, is 0-2;

p is 1 or 2;

q is 0-2; and r, at each occurrence, is 0-2.

In one embodiment, compounds of the present invention, or a stereoisomer or pharmaceutically acceptable salt from thereof, are those in which:

Ring A is

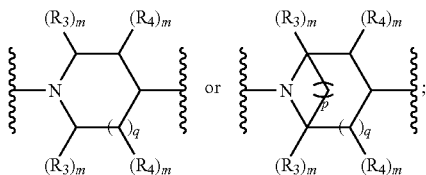

T is

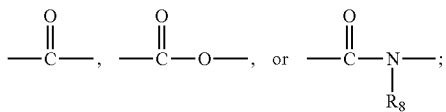

V is a bond, —$(CR_8R_8)_p$—,

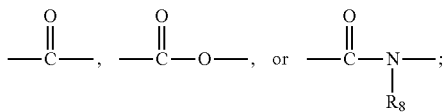

$R_1$ is aryl or heteroaryl, both of which may be optionally substituted with one or more $R_{1a}$;

$R_{1a}$ is halo, —CN, alkyl, haloalkyl, —O-alkyl or —O-haloalkyl;

$R_2$ is alkyl or cycloalkyl, wherein the alkyl may be optionally substituted with —OH;

$R_3$, at each occurrence, is alkyl; or any two $R_3$'s attached to the same carbon atom may form a 3- to 6-membered ring;

$R_4$, at each occurrence, is F, alkyl, —$OR_9$ or —$NR_9R_9$; or any two alkyl $R_4$'s attached to the same carbon atom may form a 3- to 6-membered ring;

$R_5$ is alkyl, cycloalkyl, aryl, heterocyclyl or heteroaryl, all of which may be optionally substituted with one or more $R_{5a}$;

$R_{5a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$S(O)_3H$, —C(=O)$NR_9R_9$, —$NR_9R_9$, —$S(O)_2NR_9R_9$, —$NR_9S(O)_2(CF_2)_rCF_3$, —C(=O)$NR_9S(O)_2R_6$, —$S(O)_2NR_9C(=O)OR_6$, —$S(O)_2NR_9C(=O)NR_9R_9$, —C(=O)$NR_9S(O)_2(CF_2)_rCF_3$, —C(=O)(CR_8R_8)_rR_{10}$, —$NR_9C(=O)H$, —$NR_9C(=O)(CR_8R_8)_rR_{10}$, —$NR_9C(=O)NR_9R_9$, —OC(=O)(CR_8R_8)_rR_{10}$, —S(=O)(CR_8R_8)_rR_{10}$, —$S(O)_2(CR_8R_8)_rR_{10}$, —$NR_9C(=O)OR_8$, —$NR_9S(O_2)R_8$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{5b}$;

$R_{5b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —$S(O)_3H$, —C(=O)$NR_9R_9$, —$NR_9R_9$, —$S(O)_2NR_9R_9$, —$NR_9S(O)_2(CF_2)_rCF_3$, —C(=O)$NR_9S(O)_2R_6$, —$S(O)_2NR_9C(=O)OR_6$, —$S(O)_2NR_9C(=O)NR_9R_9$, —C(=O)$NR_9S(O)_2(CF_2)_rCF_3$, —C(=O)(CR_8R_8)_rR_{10}$, —$NR_9C(=O)H$, —$NR_9C(=O)(CR_8R_8)_rR_{10}$, —$NR_9C(=O)NR_9R_9$, —OC(=O)(CR_8R_8)_rR_{10}$, —S(=O)_2(CR_8R_8)_rR_{10}$, —$S(O)_2(CR_8R_8)_rR_{10}$, —$NR_9C(=O)OR_8$, —$NR_9S(O_2)R_8$, aryloxy or arylalkyl;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl, —C(=O)$R_{15}$, —C(=O)$NR_8R_{15}$, —C(=O)$OR_{15}$ or heterocyclylalkyl, wherein the aryl, arylalkyl, heteroaryl, heteroarylalkyl, heterocyclyl or heterocyclylalkyl may be optionally substituted with one or more $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —C(=O)$NR_{14}R_{14}$, —$NR_{14}R_{14}$, —$S(O)_2NR_{14}R_{14}$, —$NR_{14}S(O)_2(CF_2)_rCF_3$, —C(=O)$NR_{14}S(O)_2R_6$, —$S(O)_2NR_{14}C(=O)OR_6$, —S(O)_2NR_{14}C(=O)NR_{14}R_{14}$, —C(=O)$NR_{14}S(O)_2(CF_2)_rCF_3$, —C(=O)(CR_8R_8)_rR_{14}$, —$NR_{14}C(=O)H$, —$NR_{14}C(=O)(CR_8R_8)_rR_{14}$, —OC(=O)(CR_8R_8)_rR_{14}$, —S(=O)(CR_8R_8)_rR_{14}$, —$S(O)_2(CR_8R_8)_rR_{14}$, —$NR_{14}C(=O)OR_8$, —$NR_{14}S(O_2)R_8$, aryloxy or arylalkyl;

$R_{10}$, at each occurrence, is independently selected from alkyl, alkenyl, alkynyl, aryl, arylalkyl, heterocyclyl or heterocyclylalkyl, wherein the aryl, arylalkyl, heterocyclyl or heterocyclylalkyl may be optionally substituted with one or more $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —$S(O)_3H$, —C(=O)$NR_{14}R_{14}$, —$NR_{14}R_{14}$, —$S(O)_2NR_{14}R_{14}$, —$NR_{14}S(O)_2(CF_2)_rCF_3$, —$C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —$C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$S(=O)(CR_8R_8)_rR_{14}$, —$S(O)_2(CR_8R_8)_rR_{14}$, —$NR_{14}C(=O)OR_8$, —$NR_{14}S(O_2)R_8$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl;

m, at each occurrence, is 0-2;

p is 1 or 2;

q is 0-2; and r, at each occurrence, is 0-2.

In another embodiment, compounds of the present invention, or a stereoisomer or pharmaceutically acceptable salt from thereof, are those in which:

Ring A is

T is

V is a bond, —$(CR_8R_8)_p$—, $R_1$ is aryl or heteroaryl, both of which may be optionally substituted with one or more $R_{1a}$;

$R_{1a}$ is halo, —CN, alkyl, haloalkyl, —O-alkyl or —O-haloalkyl;

$R_2$ is alkyl or cycloalkyl, wherein the alkyl may be optionally substituted with —OH;

$R_3$, at each occurrence, is alkyl;

$R_4$, at each occurrence, is F, alkyl, —$OR_9$ or —$NR_9R_9$;

$R_5$ is alkyl, cycloalkyl, aryl or heteroaryl, all of which may be optionally substituted with one or more $R_{5a}$;

$R_{5a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —C(=O)NR_9R_9$, —$NR_9R_9$, —$S(O)_2NR_9R_9$, —$NR_9S(O)_2(CF_2)_rCF_3$, —C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —C(=O)(CR_8R_8)_rR_{10}$, —$NR_9C(=O)H$, —$NR_9C(=O)(CR_8R_8)_rR_{10}$, —$NR_9C(=O)NR_9R_9$, —$OC(=O)(CR_8R_8)_rR_{10}$, —$S(=O)(CR_8R_8)_rR_{10}$, —$S(O)_2(CR_8R_8)_rR_{10}$, —$NR_9C(=O)OR_8$, —$NR_9S(O_2)R_8$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{5b}$;

$R_{5b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{10}$, —$O(CF_2)_rCF_3$, —$O(CR_8R_8)_rR_{10}$, —OH, —SH, —$S(CR_8R_8)_rR_{10}$, —C(=O)NR_9R_9$, —$NR_9R_9$, —$S(O)_2NR_9R_9$, —$NR_9S(O)_2(CF_2)_rCF_3$, —C(=O)NR_9S(O)_2R_6$, —$S(O)_2NR_9C(=O)OR_6$, —$S(O)_2NR_9C(=O)NR_9R_9$, —$C(=O)NR_9S(O)_2(CF_2)_rCF_3$, —C(=O)(CR_8R_8)_rR_{10}$, —$NR_9C(=O)H$, —$NR_9C(=O)(CR_8R_8)_rR_{10}$, —$NR_9C(=O)NR_9R_9$, —$OC(=O)(CR_8R_8)_rR_{10}$, —$S(=O)(CR_8R_8)_rR_{10}$, —$S(O)_2(CR_8R_8)_rR_{10}$, —$NR_9C(=O)OR_8$, —$NR_9S(O_2)R_8$, aryloxy or arylalkyl;

$R_6$, at each occurrence, is independently alkyl, cycloalkyl, cycloalkylalkyl, aryl, arylalkyl or heteroaryl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl, —$C(=O)R_{15}$, —$C(=O)OR_{15}$ or heterocyclylalkyl, wherein the aryl, arylalkyl, heteroaryl, heteroarylalkyl, heterocyclyl or heterocyclylalkyl may be optionally substituted with one or more $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —C(=O)NR_{14}R_{14}$, —$NR_{14}R_{14}$, —$S(O)_2NR_{14}R_{14}$, —$NR_{14}S(O)_2(CF_2)_rCF_3$, 13(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$S(=O)(CR_8R_8)_rR_{14}$, —$S(O)_2(CR_8R_8)_rR_{14}$, —$NR_{14}C(=O)OR_8$, —$NR_{14}S(O_2)R_8$, aryloxy or arylalkyl;

$R_{10}$, at each occurrence, is independently selected from alkyl, alkenyl, aryl, arylalkyl, heterocyclyl or heterocyclylalkyl, wherein the aryl, arylalkyl, heterocyclyl or heterocyclylalkyl may be optionally substituted with one or more $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR_8R_8)_rR_{14}$, —$O(CF_2)_rCF_3$, —$O(CR_8R_8)_rR_{14}$, —OH, —SH, —$S(CR_8R_8)_rR_{14}$, —C(=O)NR_{14}R_{14}$, —$NR_{14}R_{14}$, —$S(O)_2NR_{14}R_{14}$, —$NR_{14}S(O)_2(CF_2)_rCF_3$, —C(=O)NR_{14}S(O)_2R_6$, —$S(O)_2NR_{14}C(=O)OR_6$, —$S(O)_2NR_{14}C(=O)NR_{14}R_{14}$, —$C(=O)NR_{14}S(O)_2(CF_2)_rCF_3$, —C(=O)(CR_8R_8)_rR_{14}$, —$NR_{14}C(=O)H$, —$NR_{14}C(=O)(CR_8R_8)_rR_{14}$, —$OC(=O)(CR_8R_8)_rR_{14}$, —$S(=O)(CR_8R_8)_rR_{14}$, —$S(O)_2(CR_8R_8)_rR_{14}$, —$NR_{14}C(=O)OR_8$, —$NR_{14}S(O_2)R_8$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl;

m, at each occurrence, is 0-2;

p is 1 or 2;

q is 0-2; and r, at each occurrence, is 0-2.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

In another embodiment, the present invention provides a compound of the present invention for use in therapy for treating an inflammatory disease.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of an inflammatory disease.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of an inflammatory disease.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat an inflammatory disease.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy*, 2602-2605 (1995).

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

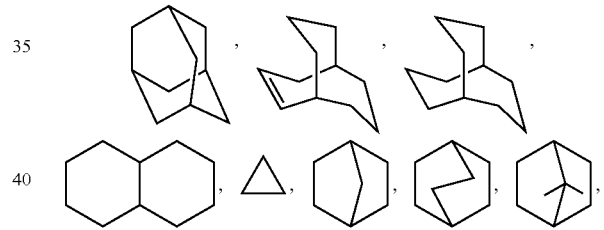

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

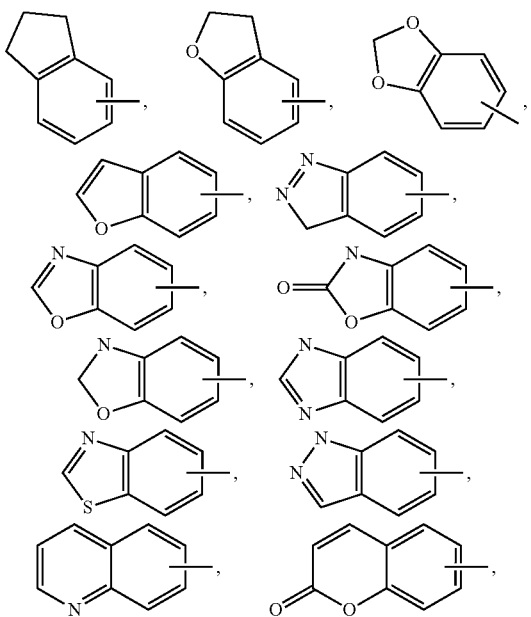

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —$NO_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmidic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., publ., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters, carbamates and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Ch. 31, Academic Press, publ. (1996);

b) Bundgaard, H., ed., *Design of Prodrugs*, Elsevier, publ. (1985);

c) Krause, B. R. et al., Chapter 6: "ACAT Inhibitors: Physiologic Mechanisms for Hypolipidemic and Anti-Atherosclerotic Activities in Experimental Animals", *Inflammation: Mediators and Pathways*, CRC Press, Inc., publ., Ruffolo, Jr., R. R. et al., eds., pp. 173-198 (1995); and d) Testa, B. et al., *Hydrolysis in Drug and Prodrug Metabolism*, Wiley-VCH, publ. (2003).

Said references are incorporated herein by reference.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention.

Compounds of the present invention can be prepared by a variety of methods well-known to one skilled in the art. As illustrated in Scheme 1, the essence of the preparation involves the synthesis of compounds analogous to compound 1.4 Such an intermediate can be derivatized by a number of very well-known methods to form amides, sulfonamides, and ureas, all of which are examples of the present invention.

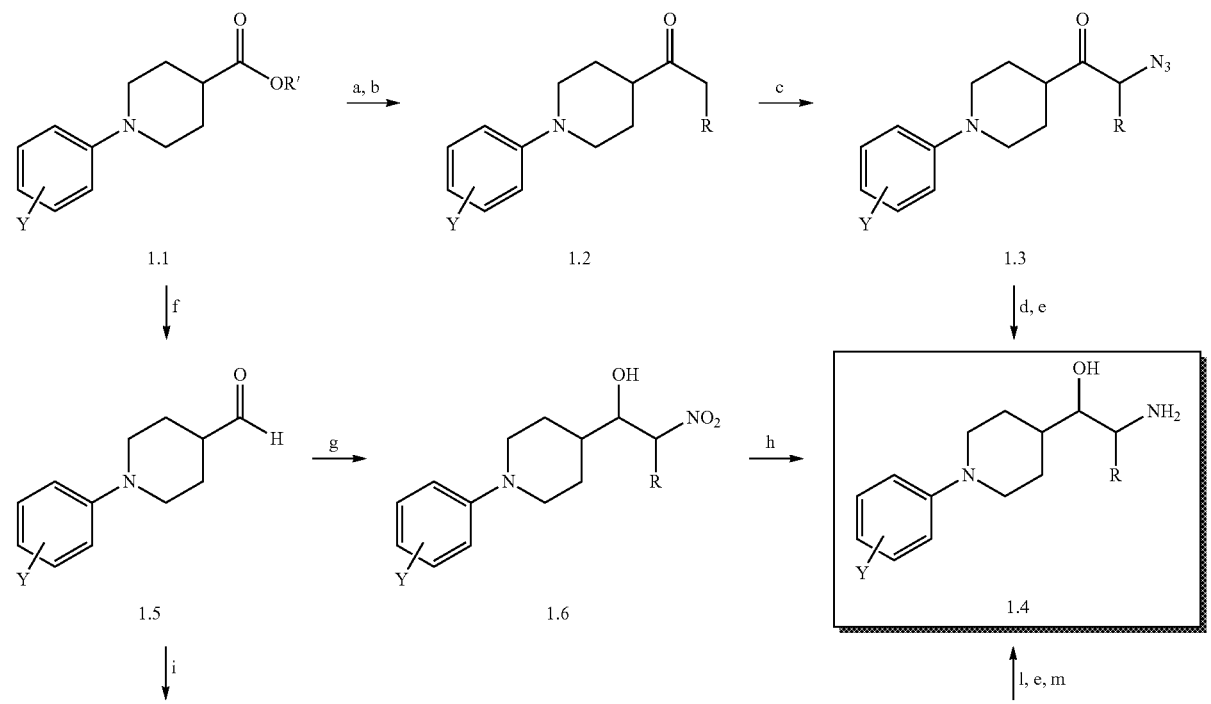

Scheme 1

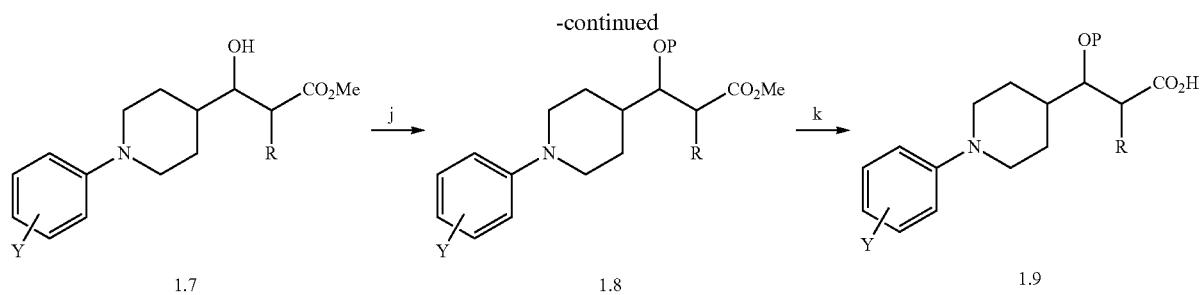

1.7           1.8           1.9

Examples of reagents: (a) Me(MeO)NH$_2$Cl, AlMe$_3$; (b) RCH$_2$MgBr; (c) TMSOTf, Et$_3$N, then NBS, then NaN$_3$; (d) NaBH$_4$, MeOH; (e) H$_2$, Pd/C; (f) DIBAL-H; (g) RCH$_2$NO$_2$, NaOH; (h) NiCl$_2$, NaBH$_4$; (i) RCH$_2$CO$_2$Me, LDA; (j) TBSCl, Im (P = tBuMe$_2$Si); (k) LiOH, THF/MeOH/H$_2$O; (l) (PhO$_2$)P(O)N$_3$, NEt$_3$, then BnOH; (m) TBAF (P = tBuMe$_2$Si).

Starting from 1.1, which may be easily synthesized via N-arylation of the alkyl isonipecotate, one can proceed via the ketone 1.2 to ketoazide 1.3. This, in turn, may be reduced in a stepwise fashion to provide 1.4. Alternatively, one can synthesize the aldehyde 1.5 from 1.1, and then proceed via a Henry reaction to give 1.6. This material is readily reduced to provide the targeted intermediate 1.4. Still differently, one could proceed via an aldol addition of the aldehyde to afford beta-hydroxyester 1.7, which can be protected and hydrolyzed in a stepwise fashion to provide the acid 1.9. This material can be rearranged under the conditions of Curtius to afford the doubly protected aminoalcohol, which can be deprotected to afford the targeted 1.4. Each of these routes offers the experimentalist alternative strengths, depending on whether one wishes to maximize speed (via the Henry reaction), diversity at "R" (alpha-azidation route), or stereochemical control (via the aldol route).

Other features of the invention will become apparent in the course of the following descriptions of exemplary embodiments that are given for illustration of the invention and are not intended to be limiting thereof.

EXAMPLES

Abbreviations used in the Examples are defined as "2×" for twice, "3×" for thrice, "° C." for degrees Celsius, "g" for gram or grams, "mmol" for millimolar, "mL" for milliliter or milliliters, "M" for molar, "min" for minute or minutes, "mg" for milligram or milligrams, "h" for hour or hours, "LC" for liquid chromatography, "HPLC" for high performance liquid chromatography, "MS" for mass spectroscopy, "RT" for room temperature, "THF" for tetrahydrofuran, "Et$_2$O" for diethyl ether, "EtOAc" for ethyl acetate, "Na$_2$SO$_4$" for sodium sulfate, "CH$_2$Cl$_2$" for methylene chloride, "TFA" for trifluoroacetic acid, "sat." for saturated, "NaHCO$_3$" for sodium bicarbonate, "N" for normal, "NaOH" for sodium hydroxide, "MeOH" for methanol, "MgSO$_4$" for magnesium sulfate, "Hex" for hexane, "H$_2$O" for water, "HCl" for hydrochloric acid, "v/v" for volume to volume ratio. "D", "L", "R" and "S" are stereochemical designations familiar to those skilled in the art. Chemical names were derived using ChemDraw Ultra, version 8.0.8. When this program failed to provide a name for the exact structure in question, an appropriate name was assigned using the same methodology utilized by the program.

Example 1

N-(1-(1-(4-Chlorophenyl)piperidin-4-yl)-1-hydroxybutan-2-yl)cyclopentanecarboxamide

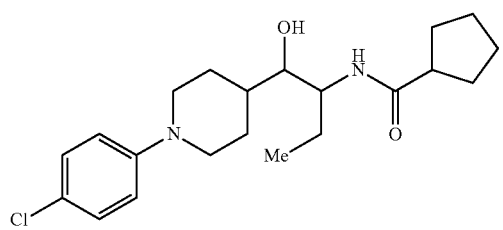 [SMILES: CCC(NC(=O)C1CCCC1)C(O)C1CCN(c2ccc(Cl)cc2)CC1]

Step 1: Benzyl 4-(methoxy(methyl)carbamoyl)piperidine-1-carboxylate

A mixture of 1-(benzyloxycarbonyl)piperidine-4-carboxylic acid (10 g, 38.0 mmol), N,O-dimethylhydroxylamine hydrochloride (5.56 g, 57.0 mmol), and CH$_2$Cl$_2$ (120 mL) was treated with 1-ethyl-3-(3-dimethylaminopropyl)carbodiimide hydrochloride (10.92 g, 57.0 mmol) and 4-(dimethylamino)pyridine (0.464 g, 3.80 mmol). The mixture was cooled in an ice bath and treated with N,N-diisopropylethylamine (13.23 mL, 76 mmol) over 3 min. After 10 min, the cooling bath was removed and the mixture was stirred at RT overnight (~14 h). The mixture was diluted with CH$_2$Cl$_2$ (150 mL), washed with saturated NaHCO$_3$ (3×50 mL), 2 M HCl (2×50 mL) and brine, dried over MgSO$_4$, and concentrated to provide a residue. The residue was purified by flash chromatography using a 120 g silica gel cartridge and 10:1 Hex/EtOAc to elute the product. The fractions containing the product were pooled and concentrated on a rotary evaporator to give the title compound (7.8 g, 25.5 mmol, 67% yield) as a pale yellow oil. LC-MS: 307.1, (M+H)$^+$. $^1$H-NMR (400 MHz, CDCl$_3$) δ ppm 7.25-7.37 (5H, m), 5.11 (2H, s), 4.21 (2H, s), 3.66-3.71 (3H, m), 3.16 (3H, s), 2.83 (3H, d, J=5.93 Hz), 1.64-1.75 (4H, m).

Step 2: N-Methoxy-N-methylpiperidine-4-carboxamide

A solution of benzyl 4-(methoxy(methyl)carbamoyl)piperidine-1-carboxylate (5.0 g, 16.32 mmol) in absolute EtOH (75 mL) was charged with 10% Pd-carbon (500 mg). The flask was evacuated and backfilled with hydrogen. The mixture was stirred for 60 h under 1 atmosphere of hydrogen (latex balloon). The catalyst was removed by filtration and the filtrate concentrated and azeotroped twice with MeOH (50 mL) to give the title compound (2.6 g, 15.10 mmol, 92% yield) as a pale yellow oil. LC-MS: (Waters Sunfire C18 4.6 mm×30 mm). 313.20, [M+H]; $t_R$=0.12 min; 2 min gradient from 10/90/0.1 MeOH/H$_2$O/TFA to 90/10/0.1 MeOH/H$_2$O/TFA at 5 mL/min flow rate. $^1$H-NMR (400 MHz, CDCl$_3$) δ ppm 3.65 (3H, s), 3.12 (3H, s), 3.08 (2H, dt, J=12.59, 3.27 Hz), 2.76 (1H, s), 2.61 (2H, td, J=12.21, 3.27 Hz), 1.57-1.69 (5H, m).

Step 3: 1-(4-Chlorophenyl)-N-methoxy-N-methylpiperidine-4-carboxamide

A flask containing 2-(2'-di-tent-butylphosphine)biphenylpalladium(II) acetate (0.927 g, 2.003 mmol) and potassium tert-butoxide (1.798 g, 16.03 mmol) was flushed with nitrogen and then charged with 4-bromochlorobenzene (3.07 g, 16.03 mmol), N-methoxy-N-methylpiperidine-4-carboxamide (2.3 g, 13.35 mmol) and anhydrous toluene (25 mL). The resulting mixture was stirred under nitrogen at 100° C. for 1.5 h. After this time, the reaction mixture was cooled to room temperature, diluted with ether (200 mL), washed with water and brine, dried over MgSO$_4$ and concentrated to yield a residue. The residue was purified by flash chromatography using a 120 g silica gel cartridge and an eluent gradient from 10:1 Hex/EtOAc to 2:1 EtOAc/Hex. The fractions containing the product were pooled and concentrated on a rotary evaporator to the title compound (2.2 g, 7.78 mmol, 58.3% yield) as a yellow-green solid. LC-MS: (Waters Sunfire C18 4.6 mm×50 mm). 283.19, [M+H]; $t_R$=1.79 min; 4 min gradient from 10/90/0.1 MeOH/H$_2$O/TFA to 90/10/0.1 MeOH/H$_2$O/TFA at 4 mL/min flow rate. $^1$H NMR (400 MHz, CDCl$_3$) δ ppm 7.13-7.21 (2H, m), 6.81-6.87 (2H, m), 3.72 (3H, s), 3.69 (1H, t, J=3.30 Hz), 3.66 (1H, t, J=2.86 Hz), 3.19 (3H, s), 2.70-2.82 (3H, m), 1.82-1.94 (4H, m).

Step 4: 1-(4-Chlorophenyl)piperidine-4-carbaldehyde

A solution of 1-(4-chlorophenyl)-N-methoxy-N-methylpiperidine-4-carboxamide (200 mg, 0.707 mmol) in anhydrous THF (2 mL) was placed under nitrogen, cooled to −78° C., and treated with diisobutylaluminum hydride (1.061 mL of a 1.0 M solution in toluene, 1.061 mmol). The reaction mixture was stirred at −78° C. for 1 h. After this time, the reaction mixture was quenched with 10% Rochelle's salt and warmed to RT before being extracted several times with Et$_2$O. The extract was dried over MgSO$_4$ and concentrated to give the title compound (167 mg, 106% yield) as a yellow oil, which was used in the subsequent step without additional purification. $^1$H NMR (400 MHz, CDCl$_3$) δ ppm 9.69 (1H, s), 7.16-7.21 (2H, m), 6.81-6.88 (2 H, m), 3.55 (2H, ddd, J=12.63, 3.74, 3.63 Hz), 2.80-2.87 (2H, m), 2.35-2.43 (1H, m), 1.98-2.07 (2H, m), 1.72-1.82 (2H, m).

Step 5: 1-(1-(4-Chlorophenyl)piperidin-4-yl)-2-nitrobutan-1-ol

A mixture of 1-(4-chlorophenyl)piperidine-4-carbaldehyde (157 mg, 0.7 mmol), 1-nitropropane (0.125 mL, 1.400 mmol), 0.025 M NaOH (2 mL) and MeOH (1 mL) was treated with 25% aqueous cetyltrimethylammonium chloride (0.139 mL, 0.105 mmol). The reaction mixture was sonicated at RT for 4 h, and then stirred at RT for 14 h. After this time, the mixture was treated with brine and extracted with diethyl ether. The extract was dried over MgSO$_4$ and concentrated to yield a residue. The residue was purified by flash chromatography on silica gel, eluting with 15-25% EtOAc/hexanes to give the diastereomeric mixture (2:1 more polar/less polar on reverse-phase HPLC) of the title compound (75 mg, 0.240 mmol, 34.3% yield) as a clear oil. LC-MS: (Waters Sunfire C18 4.6 mm×50 mm) 313.20, [M+H]; $t_R$=1.95 min, 2.21 min; 10%-90%-0.1% MeOH/H$_2$O/TFA to 90%-10%-0.15 MeOH/H$_2$O/TFA at 1n 4 min 4 mL/min flow rate. $^1$H-NMR (400 MHz, CD$_3$OD) δ ppm 7.05-7.11 (2H, m), 6.81-6.87 (2H, m), 4.42-4.51 (1H, m), 3.67 (2H, dd, J=7.36, 3.84 Hz), 3.61 (3H, d, J=11.42 Hz), 2.51-2.62 (3H, m), 1.81-1.91 (2H, m), 1.58-1.64 (3H, m), 1.51-1.56 (2H, m).

Step 6: 2-Amino-1-(1-(4-chlorophenyl)piperidin-4-yl)butan-1-ol

A suspension of nickel chloride (29.8 mg, 0.230 mmol) in MeOH (5 mL) was sonicated for 40 min until the solid was mainly dissolved, yielding a light yellow mixture. Powdered sodium borohydride (0.041 mL, 1.151 mmol) was added to the mixture in portions in order to minimize the foaming. The resulting black mixture was sonicated for 10 min. After this time, a solution of 1-(1-(4-chlorophenyl)piperidin-4-yl)-2-nitrobutan-1-ol (72 mg, 0.230 mmol) in MeOH (1 mL) was added to the mixture. Upon completion of addition, the reaction mixture was stirred at RT for 15 min and then filtered through Celite (MeOH rinses). The filtrate was concentrated and the resultant residue was treated with saturated NaHCO$_3$ (5 mL) and 1 M NaOH (10 mL). The resulting mixture was extracted with CH$_2$Cl$_2$ (3×20 mL). The extract was washed with brine, dried over MgSO4 and concentrated to give the title compound (37.8 mg, 0.134 mmol, 58% yield) as a diastereomeric mixture. LC/MS [M+H]$^+$=283.26. HPLC $t_R$=1.21 min. [Waters Sunfire C18 4.6×50 mm column, 4 min gradient from 10/90/0.1 MeOH/H$_2$O/TFA to 90/10/0.1 MeOH/H$_2$O/TFA at 4 mL/min flow rate]. $^1$H-NMR (400 MHz, CDCl$_3$) δ ppm 7.08 (2H, d, J=9.01 Hz), 6.84 (2H, d, J=8.79 Hz), 3.59 (2H, t, J=9.89 Hz), 3.35 (1H, d, J=6.59 Hz), 3.15 (1H, d, J=11.42 Hz), 3.08 (1H, dd, J=6.59, 4.17 Hz), 2.52-2.64 (2H, m), 1.87 (1H, d, J=12.52 Hz), 1.74 (1H, d, J=14.50 Hz), 1.13-1.69 (5H, m), 0.89 (2H, ddd, J=14.28, 7.47, 7.25 Hz).

Step 7: Example 1

A solution of 2-amino-1-(1-(4-chlorophenyl)piperidin-4-yl)butan-1-ol (56 mg, 0.198 mmol), cyclopentanecarboxylic acid (0.024 mL, 0.218 mmol), N,N-diisopropylethylamine (0.069 mL, 0.396 mmol), and O-benzotriazol-1-yl-N,N,N',N'-tetra-methyluronium tetrafluoroborate (76 mg, 0.238 mmol) in DMF (1.5 mL) was stirred at RT for 4 h. After this time, the reaction mixture was concentrated on a rotary evaporator, and the resultant residue was partitioned between EtOAc and saturated NaHCO$_3$. The organic phase was washed sequentially with sat. NaHCO$_3$ and brine, dried over Na$_2$SO$_4$ and then concentrated in vacuo to yield the crude product. The crude product was purified by preparative reverse phase HPLC {Waters Sunfire C-18 19×100 mm; 10 ml/min flow; gradient: (0, 10 min), (0% B, 100% B); solvent B=90:10 MeOH/H$_2$O, 0.1% TFA; solvent A=90:10 H$_2$O/MeOH, 0.1% TFA} to provide Example 1 (16 mg). LC-MS: (Waters Sunfire C18 4.6 mm×50 mm) 379.31, [M+H]; $t_R$=2.38 min; 4 min gradient from 10/90/0.1 MeOH/H$_2$O/TFA to 90/10/0.1 MeOH/H$_2$O/TFA at 4 mL/min flow rate. $^1$H-NMR (400 MHz, CD$_3$OD) δ ppm 7.25-7.67 (4H, m), 3.83-4.08 (1H, m), 3.55-3.84 (2H, m), 3.19-3.44 (2H, m), 2.70 (1H, dq, J=8.13, 7.91 Hz), 2.22 (2H, dd, J=9.67 Hz), 1.82-2.00 (2H, m), 1.68-1.81 (4H, m), 1.53-1.68 (8H, m), 0.92 (3H, t, J=7.47 Hz).

Example 2

N-(1-(1-(4-Chlorophenyl)piperidin-4-yl)-1-hydroxybutan-2-yl)cyclopentanecarboxamide

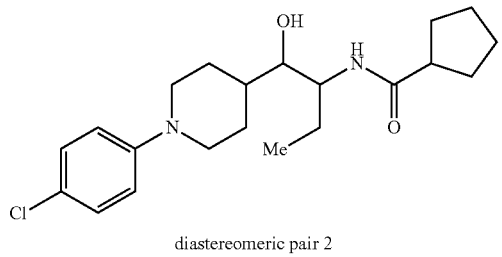 [SMILES: CCC(NC(=O)C1CCCC1)C(O)C1CCN(c2ccc(Cl)cc2)CC1]

diastereomeric pair 2

Example 2 was co-synthesized during Example 1, Step 7 and was isolated by preparative HPLC (5 mg). LC-MS: (Waters Sunfire C18 4.6 mm×50 mm) 379.31, [M+H]; $t_R$=2.46 min; 4 min gradient from 10/90/0.1 MeOH/H$_2$O/TFA to 90/10/0.1 MeOH/H$_2$O/TFA at 4 mL/min flow rate. $^1$H-NMR (400 MHz, CD$_3$OD) δ ppm 7.61 (1H, d, J=9.45 Hz), 7.14-7.54 (4H, m), 3.70-3.83 (1H, m), 3.62 (2H, d, J=11.42 Hz), 3.25-3.42 (1H, m), 2.58 (1H, dq, J=8.13, 7.91 Hz), 2.07 (1H, d, J=10.77 Hz), 1.60-1.93 (12H, m), 1.41-1.56 (2H, m), 1.19-1.41 (1H, m), 0.83 (3H, t, J=7.36 Hz).

Utility

In general, compounds of the present invention, such as particular compounds disclosed in the preceding examples, have been shown to be modulators of chemokine receptor activity (for example, by displaying Ki values <10,000 nM in a binding assay such as those set forth below). By displaying activity as modulators of chemokine receptor activity, compounds of the present invention are expected to be useful in the treatment of human diseases associated with chemokines and their cognate receptors.

Antagonism of MIP-1α Binding to Human THP-1 Cells

Compounds of the present invention have activity in the antagonism of MIP-1α binding to human THP-1 cells described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration of compound, is combined with 50 μl of $^{125}$-I labeled human MIP-1α (to give a final concentration of 50 pM radioligand) and 50 μl of binding buffer containing 5×10$^5$ cells. Cells used for such binding assays can include the THP-1 cell line, which expresses the endogenous CCR1 receptor, or human peripheral blood mononuclear cells, isolated by Ficoll-Hypaque gradient centrifugation, or human monocytes (Weiner et al., *J. Immunol. Methods*, 36:89 (1980)). The mixture of compound, cells and radioligand is incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted.

The percent inhibition of binding is calculated using the total counts obtained in the absence of any competing compound and the background binding determined by addition of 100 nM MIP-1α in place of the test compound.

Compounds of the present invention were tested in the assay described immediately above and the results shown in Table 1 below were obtained.

TABLE 1

| Example | CCR1 Binding Ki (n = 1 unless otherwise noted) |
|---------|------------------------------------------------|
| 1       | 930                                            |
| 2       | 354                                            |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisakis* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound which is N-(1-(1-(4-Chlorophenyl)piperidin-4-yl)-1-hydroxybutan-2-yl)cyclopentanecarboxamide, or a stereoisomer or pharmaceutically acceptable salt form thereof.

2. A pharmaceutical composition comprised of a pharmaceutically acceptable carrier and a therapeutically effective amount of a compound of claim 1.

\* \* \* \* \*